US00PP34678P2

(12) United States Plant Patent
Noack

(10) Patent No.: US PP34,678 P2
(45) Date of Patent: Oct. 25, 2022

(54) SHRUB ROSE PLANT NAMED 'NOA20059'

(50) Latin Name: *Rosa hybrida*
Varietal Denomination: 'NOA20059'

(71) Applicant: Reinhard Noack, Gutersloh (DE)

(72) Inventor: Reinhard Noack, Gutersloh (DE)

( * ) Notice: Subject to any disclaimer, the term of this patent is extended or adjusted under 35 U.S.C. 154(b) by 0 days.

(21) Appl. No.: 17/550,603

(22) Filed: Dec. 14, 2021

(51) Int. Cl.
*A01H 5/02* (2018.01)
*A01H 6/74* (2018.01)

(52) U.S. Cl.
USPC ..... Plt./108
CPC ..... *A01H 6/749* (2018.05)

(58) Field of Classification Search
USPC ..... Plt./108
CPC ..... A01H 5/0222
See application file for complete search history.

*Primary Examiner* — Kent L Bell
(74) *Attorney, Agent, or Firm* — Cassandra Bright

(57) ABSTRACT

A new and distinct cultivar of *Rosa* plant for garden use named 'NOA20059' is disclosed, characterized by semi-double brilliant red flowers on plants with rapid re-flowering. Plants have excellent resistance to blackspot, powdery mildew, downy mildew and rust diseases. Plants are dense and compact with uniform growth and are well suited for landscape use, especially as a groundcover. The new variety is a *Rosa,* normally produced as an outdoor garden or container plant.

1 Drawing Sheet

Latin name of the genus and species: *Rosa hybrida.*
Variety denomination: 'NOA20059'.

BACKGROUND OF THE INVENTION

The new *Rosa* cultivar is a product of a planned breeding program conducted by the inventor, Reinhard Noack, conducted in Gutersloh, Germany. The objective of the breeding program was to create new and distinct landscape rose plants with unique qualities such as a dense, compact plant habit and excellent resistance to diseases encountered in landscapes and gardens. These objectives have been substantially achieved and in that distinguish 'NOA20059' from all other varieties of which the inventor is aware. This combination of qualities is not present in prior rose cultivars known to the inventor. The cross resulting in this new variety was made during May of 2007.

The seed parent is an unpatented, proprietary *Rosa hybrida* named 'Noazauber'. The pollen parent is an unpatented, unnamed proprietary *Rosa hybrida*. The new variety was selected in April of 2008 by the inventor in a group of seedlings resulting from the 2007 crossing, in a research greenhouse in Gutersloh, Germany.

Asexual reproduction of the new cultivar was performed by terminal semi-soft wood vegetative cuttings. This was first performed at a research greenhouse in Gutersloh, Germany in Summer of 2008 and has shown that the unique features of this cultivar are stable and reproduced true to type in successive generations.

SUMMARY OF THE INVENTION

The cultivar 'NOA20059' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NOA20059' These characteristics in combination distinguish 'NOA20059' as a new and distinct *Rosa* cultivar:

1. Abundant small brilliant red flowers.
2. Dense, compact plant habit.
3. Plants have excellent resistance to blackspot, powdery mildew, downy mildew and rust diseases.
4. Plants reflower quickly
5. Long lasting individual flowers.
6. Uniform growth.
7. Easy to grow.

Plants of the new cultivar 'NOA20059' are similar to plants of the seed parent, in most horticultural characteristics, however, plants of the new cultivar 'NOA20059' differ in the following:

1. The new variety has red flowers; the seed parent has white flowers.
2. The new variety has a semi-double flower; the seed parent has a fully double flower.
3. The new variety produces flowers with a diameter on average of 4 cm; the seed parent produces flowers with an average diameter of 2.5 cm to 3.0 cm.

Plants of the new cultivar 'NOA20059' are similar to plants of the pollen parent in most horticultural characteristics, however, plants of the new cultivar 'NOA20059' differ in the following;

1. Height of the new variety is approximately 50 cm; height of the pollen parent is approximately 30 cm.
2. Plants of the new variety have very good resistance to diseases typical of garden roses; plants of the pollen parent have average resistance to the same diseases.
3. Flowers of the new variety are semi-double; flowers of the pollen parent are single.

COMMERCIAL COMPARISON

Plants of the new cultivar 'NOA20059' can be compared to the commercial variety *Rosa* 'Noare', U.S. Plant Pat. No.

11,308. These varieties are similar in most horticultural characteristics, however 'NOA20059' differs in the following:

1. The new variety has semi-double flowers; this comparator has single flowers.
2. Plants of 'NOA20059' are more upright than plants of 'Noare'

Plants of the new cultivar 'NOA20059' can also be compared to the commercial variety *Rosa* 'Flower Carpet White' U.S. Plant Pat. No. 9,573. These varieties are similar in most horticultural characteristics; however, 'NOA20059' differs in the following:

1. The new variety has red flowers; this comparator has white flowers.
2. Flowers of 'NOA20059' are smaller in diameter than flowers of this comparator.

BRIEF DESCRIPTION OF THE PHOTOGRAPH

The accompanying photograph illustrates in full color a typical plant of 'NOA20059'. Age of the plant photographed is approximately 3 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'NOA20059' plants grown outdoors, in Gutersloh, Germany. The growing temperature ranged from approximately −1° C. to 35° C. during the day and from approximately −16° C. to 20° C. during the night. General light conditions are bright, normal sunlight. Measurements and numerical values represent averages of typical plant types.
Botanical classification: *Rosa* 'NOA20059'.
Commercial classification: Groundcover rose.

PROPAGATION

Time to initiate roots: About 42 days at approximately 20° C.
Time to produce a rooted cutting: About 90 days at approximately 15° C.

PLANT

Age of plant described: Approximately 3 years, planted in the ground.
Growth habit: Upright.
Mature height: 50 cm.
Mature plant spread: 50 cm.
Rootstock: Own root.
Growth rate: Approximately 50 cm per year.
Branching characteristics: Sympodial branching.
Length of primary lateral branches: Average 45 cm.
Diameter of lateral branches: Approximately 6 mm.
Quantity of lateral branches: Approximately 10-15.
Branching arrangement: Alternate.
Branches-young wood:
- *Diameter.*—Approximately 4 to 6 mm.
- *Texture.*—Glabrous.
- *Color.*—Near Green 143D, weakly flushed with anthocyanin Greyed-Purple 187A.

Branches-old wood:
- *Diameter.*—Approximately 1.5 cm, after 3 years.
- *Color.*—Near Green RHS 137C, with brown tinge not accurately described with RHS chart.
- *Texture.*—Smooth.
- *Approximately density/quantity of thorns.*—Dense, fine prickle-like thorns.

Thorns:
- *Density.*—Sparse, about 6 to 8 per stem.
- *Color.*—Near Greyed-Orange 176B.
- *Shape.*—Deltate.

FOLIAGE

Leaf:
- *Arrangement.*—Alternate.
- *Quantity.*—Approximately 24 per main branch.
- *Average length.*—Approximately 12 cm.
- *Average width.*—Approximately 7 cm.

Leaflet:
- *Quantity.*—Most commonly 5 to 7 per leaf. Occasionally 3.
- *Average length.*—Approximately 5.5 cm.
- *Average width.*—Approximately 2.5 cm.
- *Shape of blade.*—Ovate.
- *Apex.*—Acuminate.
- *Base.*—Obtuse.
- *Margin.*—Serrated.
- *Appearance of top surface.*—Weak to moderately glossy.
- *Appearance of bottom surface.*—Matte.
- *Texture of top surface.*—Non-pubescent.
- *Texture of bottom surface.*—Non-pubescent.
- *Leaf internode length.*—Average 3 to 5 cm.
- *Color.*—Young foliage upper side: Near Yellow-Green RHS 144B. Weak anthocyanin near Greyed-Orange N172D, strongest on very young foliage. Young foliage under side: Near Yellow-Green RHS 144C. Weak anthocyanin near Greyed-Orange N172D, strongest on very young foliage. Mature foliage upper side: Near Green RHS 137A. Mature foliage under side: Near Green RHS 137B. Venation: Type: Pinnate. Venation color upper side: Near Green 143C. Venation color under side: Near Yellow-Green 144C.

Petiole:
- *Average length.*—Approximately 2.5 cm.
- *Average diameter.*—Approximately 5 mm.
- *Color.*—Near RHS Yellow-Green 144B.
- *Texture.*—Glabrous, matte.

Rachis:
- *Average length.*—Average range 8.0 to 10.0 cm.
- *Average diameter.*—Approximately 5 mm.
- *Texture.*—Glabrous.
- *Color.*—Near RHS Yellow-Green 144B.

Stipule:
- *Shape.*—Adnate.
- *Margin.*—Amplexicaul.
- *Apex.*—Tapering.
- *Base.*—Truncate.
- *Average length.*—Average range 2.0 cm.
- *Average diameter.*—Approximately 1.0 cm.
- *Texture.*—Glabrous.
- *Color.*—Near RHS Yellow-Green 144B.

FLOWER

Natural flowering season: Spring until mid-Fall.
Begins flowering after how many years/months: As early as 3 months from a rooted liner.
Inflorescence type and habit: Semi-double whorled flowers occurring 3 to 7 per flowering node. Flowers weakly upwardly cupped, having a mostly flat profile. Flowers semi-hemispherical in shape.
Rate of flower opening: Approximately 5 days from bud to fully opened flower.
Lastingness of individual flower: 6 to 8 weeks.
Individual flower size:
*Diameter.*—Approximately 4 cm.
*Depth.*—Approximately 2.5 cm.
Pedicel:
*Length.*—About 4 to 5 cm.
*Diameter.*—4 mm.
*Texture.*—Glabrous.
*Color.*—Near RHS Yellow-Green 144B, lightly flushed Greyed-Orange N167B.
Petals:
*Petal arrangement.*—Semi-double whorl, overlapping.
*Size.*—Length: Average 1.5 cm. Width: Average 1.7 to 2 cm.
*Shape.*—Obovate.
*Margin.*—Entire, non-ruffled.
*Apex.*—Obtuse, rounded, very shallow, broad irregular lobes.
*Base.*—Obtuse.
*Petal quantity.*—Average range 13 to 26.
*Texture.*—Smooth.
Color: Petals:
*When opening.*—Upper surface: Near RHS Red 53B, base near Red 44A. Lower surface: Near RHS Red 53B, base near Red 44A.
*Fully opened.*—Upper surface: Near RHS Red 53B, base near Red 44A. Lower surface: Near RHS Red 53B, base near Red 44A.
Bud:
*Shape.*—Ovate.
*Length.*—Approximately 2 cm.
*Diameter.*—Approximately 1 cm.
*Color.*—Near Yellow-Green 146B.
Sepals:
*Length.*—1.5 cm.
*Width.*—1.0 cm.
*Shape.*—Lanceolate.
*Apex.*—Apiculate.
*Margin.*—Entire.
*Color.*—Interior Surface: Near RHS Yellow-Green 144C. Exterior Surface: Near RHS Green 143C.
*Texture.*—Densely puberulent interior and exterior surfaces.
*Sepal extensions.*—Weak or absent.
*Quantity.*—Average 5 per flower.
Receptacle:
*Length.*—1.0 cm.
*Width.*—1.5 to 2.0 cm.
*Shape.*—Pitcher shaped.
*Color.*—Near RHS Green 143C.
Fragrance: Weak to none.

REPRODUCTIVE ORGANS

Stamens:
*Number.*—Approximately 40-60.
*Filament length.*—Approximately 3 mm.
*Filament color.*—Near RHS Yellow 13C.
Anthers:
*Length.*—1 mm.
*Shape.*—Narrow ovate.
*Color.*—Near Yellow 13D.
*Pollen.*—Not observed.
Pistil:
*Number.*—Approximately 10-15.
*Pistil length.*—Approximately 4 mm.
*Style.*—Length: Approximately 2 mm. Color: Light green to cream, not accurately determined with RHS chart.
*Stigma.*—Shape: Linear. Color: Light green to cream, not accurately determined with RHS chart.

OTHER CHARACTERISTICS

Seeds and fruits: Not observed to date. Fruits typically dry up, without fully forming.
Disease/pest resistance: Excellent resistance to blackspot, powdery mildew, downy mildew and rust. Average resistance to normal pests of garden roses.
Hardiness zone: USDA Zones 5 through 10.

What is claimed is:

1. A new and distinct groundcover rose plant named 'NOA20059' as herein illustrated and described.

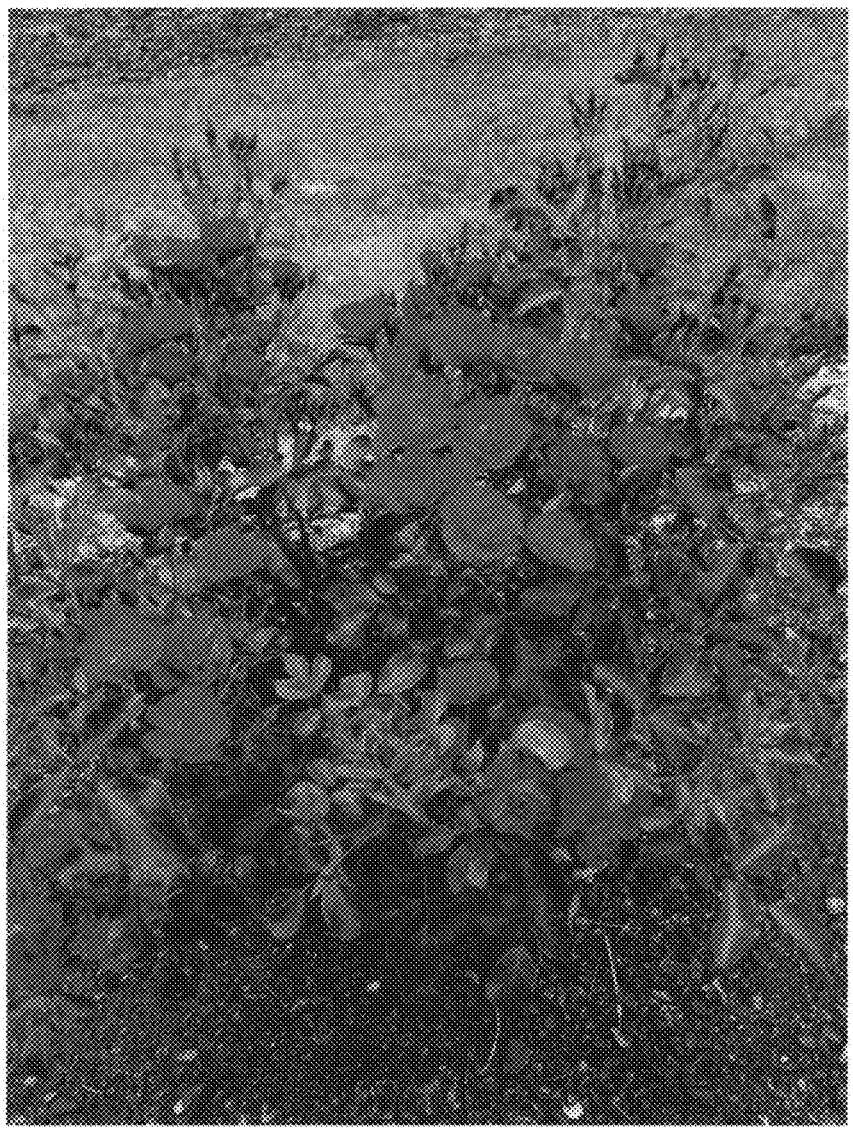

* * * * *